US012023369B2

(12) United States Patent
Oesser et al.

(10) Patent No.: US 12,023,369 B2
(45) Date of Patent: *Jul. 2, 2024

(54) USE OF COLLAGEN HYDROLYSATE FOR IMPROVING ENDURANCE PERFORMANCE AND FOR STIMULATING LIPID CATABOLISM

(71) Applicant: GELITA AG, Eberbach (DE)

(72) Inventors: Steffen Oesser, Glücksburg (DE); Stephan Hausmanns, Heidelberg (DE); Hans-Ulrich Frech, Weinheim (DE)

(73) Assignee: GELITA AG, Eberbach (DE)

( * ) Notice: Subject to any disclaimer, the term of this patent is extended or adjusted under 35 U.S.C. 154(b) by 140 days.

This patent is subject to a terminal disclaimer.

(21) Appl. No.: 17/552,499

(22) Filed: Dec. 16, 2021

(65) Prior Publication Data
US 2022/0105158 A1    Apr. 7, 2022

Related U.S. Application Data

(63) Continuation of application No. 16/285,874, filed on Feb. 26, 2019, now Pat. No. 11,235,034, which is a continuation of application No. PCT/EP2017/071184, filed on Aug. 23, 2017.

(30) Foreign Application Priority Data

Aug. 30, 2016 (DE) .......................... 102016116160.8
Feb. 14, 2017 (DE) .......................... 102017102873.0

(51) Int. Cl.
| | | |
|---|---|---|
| A61K 38/00 | (2006.01) | |
| A23L 2/00 | (2006.01) | |
| A23L 33/00 | (2016.01) | |
| A23L 33/18 | (2016.01) | |
| A61K 8/65 | (2006.01) | |
| A61K 9/00 | (2006.01) | |
| A61K 31/122 | (2006.01) | |
| A61K 31/4745 | (2006.01) | |
| A61K 35/36 | (2015.01) | |
| A61K 36/77 | (2006.01) | |
| A61K 36/82 | (2006.01) | |
| A61K 38/01 | (2006.01) | |
| A61K 38/06 | (2006.01) | |
| A61K 38/39 | (2006.01) | |
| A61K 38/44 | (2006.01) | |
| A61P 3/02 | (2006.01) | |
| A61Q 19/06 | (2006.01) | |

(52) U.S. Cl.
CPC .............. *A61K 38/39* (2013.01); *A23L 2/00* (2013.01); *A23L 33/18* (2016.08); *A23L 33/30* (2016.08); *A61K 8/65* (2013.01); *A61K 9/0053* (2013.01); *A61K 31/122* (2013.01); *A61K 31/4745* (2013.01); *A61K 35/36* (2013.01); *A61K 36/77* (2013.01); *A61K 36/82* (2013.01); *A61K 38/011* (2013.01); *A61K 38/014* (2013.01); *A61K 38/063* (2013.01); *A61K 38/446* (2013.01); *A61P 3/02* (2018.01); *A61Q 19/06* (2013.01); *A61K 2800/92* (2013.01)

(58) Field of Classification Search
CPC ........ A61K 38/39; A61K 8/65; A61K 9/0053; A61K 38/014; A23L 33/18; A23L 33/30; A61P 3/02
See application file for complete search history.

(56) References Cited

U.S. PATENT DOCUMENTS

2011/0217393 A1*  9/2011  Grise .................. A61K 38/014
424/732

FOREIGN PATENT DOCUMENTS

CN          102210855 A       10/2011

OTHER PUBLICATIONS

Study on effect of jellyfish collagen hydrolysate on anti-fatigue and anti-oxidation, Food Hydrocolloids, vol. 25, Issue 5, 2011.*
U.S. Appl. No. 16/285,874, filed Feb. 26, 2019.
Anonymous, "Hydrolysed Liquid Collagen," <naturem.co.uk/2015/11/09/hydrolysed-liquid-collagen/>, (Nov. 9, 2015).
Excerpt of ICD-10, Version: 2019, accessed online on Apr. 11, 2020 at <icd.who.int/browse10/2019/en#R53>.
Barbieri et al., "Creatine Prevents the Structural and Functional Damage to Mitochondria in Myogenic, Oxidatively Stressed C2C12 Cells and Restores Their Differentiation Capacity," *Oxidative Medicine and Cellular Longevity*, 2016: 1-12 (2016).
Bello et al., "Collagen hydrolysate for the treatment of osteoarthritis and other joint disorders: a review of the literature," *Current Medical Research Opinion*, 22(11): 2221-2232 (2008).
Bowden, "5 Amazing Benefits of Collagen Protein," <web.archive.org/web/20150729133612/http://www.myprotein.com/thezone/category/nutrition/>, (Mar. 31, 2015).
Clark et al., "24-Week study on the use of collagen hydrolysate as a dietary supplement in athletes with activity-related joint pain," *Current Medical Research Opinion*, 24(5): 1485-1496 (2008).
Ding et al., "Study on effect of jellyfish collagen hydrolysate on anti-fatigue and anti-oxidation," *Food Hydrocolloids*, vol. 25, pp. 1350-1353 (2011).
Ferron et al., "Intermittent injections of osteocalcin improve glucose metabolism and prevent type 2 diabetes in mice," *Bone*, 50(2): 568-575 (2012).
Hashizume et al., "Epigenetic regulation of the nuclear-coded GCAT and SHMT$_2$ genes confers human age-associated mitochondrial respiration defects," *Scientific Reports*, 5(10434): 1-10 (2015).

(Continued)

*Primary Examiner* — Jeanette M Lieb
(74) *Attorney, Agent, or Firm* — Leydig, Voit & Mayer, Ltd.

(57) ABSTRACT

The present invention relates to the use of collagen hydrolysate for improving endurance performance by increasing mitochondrial activity. Further, the invention relates to the use of collagen hydrolysate for stimulating lipid catabolism, and in particular for reducing body weight, by increasing mitochondrial activity.

8 Claims, 1 Drawing Sheet

(56) References Cited

OTHER PUBLICATIONS

International Bureau, International Search Report in International Application No. PCT/EP2017/071184, mailed Nov. 22, 2017.
Kitakaze et al., "The collagen derived dipeptide hydroxyprolyl-glycine promotes C2C12 myoblast differentiation and myotube hypotrophy," *Biochemical and. Biophysical Research Communications*, 478(3): 1292-1297 (2016).
Mizuno et al., "Antifatigue effects of coenzyme Q10 during physical fatigue," *Nutrition*, 24(4): 293-9 (2008).
Okiura et al., "Effects of collagen hydrolysate on the tibialis anterior muscle and femur in senescence-accelerated mouse prone 6," *Journal of Musculoskeletal and Neuronal Interactions*, 16(2): 161-167 (2016).
Porfirio et al., "Collagen supplementation as a complementary therapy for the prevention and treatment of osteoporosis and osteoarthritis: a systematic review," *Rev. Bras. Geriatr. Gerontol.*, 19(1): 153-164 (2016).
Rutschmann et al., "Recombinant expression of hydroxylated human collagen in *Escherichia coli*," *Applied Microbiology and Biotechnology*, 28(10): 4445-4455 (2013).
Schieke et al., "The Mammalian Target of Rapamycin (mTOR) Pathway Regulates Mitochondrial Oxygen Consumption and Oxidative Capacity," *Journal of Biological Chemistry*, 281(37): 27643-27652 (2006).
Zdzieblik et al., "Collagen peptides supplementation in combination with resistance training improves body composition and increases muscle strength in elderly sarcopenic men: a randomised controlled trial," *British Journal of Nutrition*, 114(8): 1237-1245 (2015).

\* cited by examiner

USE OF COLLAGEN HYDROLYSATE FOR IMPROVING ENDURANCE PERFORMANCE AND FOR STIMULATING LIPID CATABOLISM

CROSS-REFERENCE TO RELATED APPLICATIONS

This patent application is a continuation of U.S. application Ser. No. 16/285,874, filed Feb. 26, 2019, which is a continuation of International Patent Application No. PCT/EP2017/071184, filed Aug. 23, 2017, which claims the benefit of German Patent Application No. 10 2017 102 873.0, filed Feb. 14, 2017 and German Patent Application No. 10 2016 116 160.8, filed Aug. 30, 2016, which are each incorporated herein by reference.

FIELD OF THE INVENTION

The present invention relates to the use of collagen hydrolysate for improving endurance performance.

Further, the invention relates to the use of collagen hydrolysate for stimulating lipid catabolism, and in particular for reducing body weight.

BACKGROUND OF THE INVENTION

Collagen hydrolysate, which is produced in particular by the enzymatic hydrolysis of starting materials of animal origin that contain collagen, is composed of a mixture of peptides whereof the molecular weights are distributed over a particular size range, in dependence on the starting material and the production conditions. The use of collagen hydrolysate as a nutritional supplement has been known for a considerable time, in particular for preventing and/or treating bone, joint or connective tissue complaints, particularly because it has been possible to demonstrate a stimulating effect on the synthesis of the body's own extracellular matrix in these tissue types by collagen peptides (see for example Bello et al., *Curr. Med. Res. Opin.* 2006 (22) 2221-2232).

BRIEF SUMMARY OF THE INVENTION

It has now surprisingly been found that collagen hydrolysate also results in an increase in mitochondrial activity in human and animal cells, that is to say in an increase in the number of mitochondria per cell and/or an enlargement of the individual mitochondria.

From this finding it results that collagen hydrolysate according to the present invention can be used in a targeted manner to improve the endurance performance and to stimulate lipid catabolism in humans and animals by increasing mitochondrial activity in the muscle cells thereof.

DETAILED DESCRIPTION OF THE INVENTION

Figure 1A:
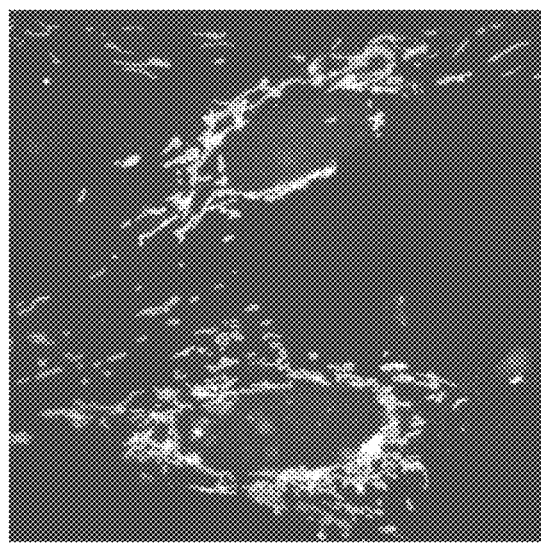
FIGS. 1A-1C show fluorescence microscopy images of SH-SY5Y cells that have been incubated in the presence of 0.05 weight % (FIG. 1A), 0.2 weight % (FIG. 1B) or 2.5 weight % (FIG. 1C) of collagen hydrolysate.

The endurance performance of the human or animal body is correlated with the capacity of the aerobic metabolism to supply the musculature with the required energy in the form of ATP (adenosine triphosphate) over a long period. An important factor in aerobic capacity is oxygen absorption, which is in turn determined by three factors: oxygen supply through the lungs, oxygen transport through the cardiovascular system, and oxygen utilisation in the muscle cells. While maximum oxygen supply is substantially predetermined by the individual anatomical circumstances (total surface area of the alveoli), oxygen transport and oxygen utilisation can be enhanced by training and other measures, wherein the last step typically represents the crucial limiting factor. For this reason, endurance performance is substantially dependent on the number of mitochondria (per muscle cell, or in the musculature overall), in which the reactions that consume oxygen and generate ATP in the respiratory chain occur.

In general, an increase in mitochondrial activity means that the metabolic rate in the body is raised, and a greater quantity of nutrients per unit time is metabolised for energy recovery. However, a higher catabolic activity necessarily results (if nutrient supply remains constant) in greater breakdown of the body's reserves, that is to say in stimulation of lipid catabolism. Here, catabolism of long-chain carboxylic acids released from the fatty tissue takes place substantially in the entire body, and in particular in the liver, so for this aspect of the invention—in contrast to improving the endurance performance—it is not only the mitochondria in the muscle cells that are relevant.

The use according to the invention of collagen hydrolysate includes in particular a non-therapeutic use, that is to say administration of collagen hydrolysate to persons or animals not medically in need of therapy as regards their endurance performance or their body weight. Rather, the use is carried out on the one hand with the objective of a general desirable enhancement of endurance performance. This can contribute to an improvement in quality of life, and is particularly relevant to sportspeople. On the other hand, a reduction in body weight as a result of stimulating lipid catabolism may be desired primarily for cosmetic reasons, that is to say to improve body proportions.

In addition, however, the invention includes the therapeutic use of collagen hydrolysate for preventing and/or treating a pathological condition characterised by a reduction in mitochondrial activity. In particular, the pathological condition may be characterised by a reduction in endurance performance and/or an increase in body weight.

In the context of this therapeutic use, the pathological condition is preferably selected from obesity, cardiovascular diseases, cardiac arrhythmia, cardiac insufficiency, hypotonicity, hypertension, metabolic disorders, diabetes mellitus, metabolic syndrome, sideroblastic anaemia, dysfunctions of the kidneys and of the liver, neuropathy, ataxia, epileptic attacks, dementia, Alzheimer's disease, autism, depression, chronic fatigue syndrome, Parkinson's disease, motor neurone disease, multiple sclerosis, stroke-like symptoms, migraine, myoclonus, palsy, neuralgia, hyperpathia, hyperaesthesia, dysphagia, vomiting, constipation, diarrhoea, degeneration of the optic nerve fibres and the retina, nystagmus, ptosis, nyctalopia, hearing loss, deafness and disorders of the inner ear. With these indications, a therapeutic effect may be achieved by increasing the number of mitochondria or the mitochondrial activity.

Because an increase in the mitochondrial activity lowers the glucose level, the administration of collagen hydrolysate may also have a positive effect in preventing and/or treating cancer, that is to say malign tumours. This is based on the observation that tumour cells are primarily supplied with the energy they require by anaerobic metabolism (lactic acid fermentation), and are necessarily dependent on glucose for this. A higher glucose consumption in the body's cells would thus weaken the tumour cells.

In the context of the invention, it has also been found that collagen hydrolysate results in greater expression of the enzyme AMP-activated protein kinase (AMPK). This regulatory enzyme likewise has an effect on the energy metabolism of the cell, so increasing the quantity of AMPK also has a positive effect on endurance performance and lipid catabolism. There may possibly be a direct correlation between the increase in mitochondrial activity brought about by collagen hydrolysate and the increase in AMPK expression.

In all the uses according to the present invention, collagen hydrolysate is preferably administered enterally, in particular orally.

In a preferred embodiment of the invention, collagen hydrolysate is administered in the form of a nutritional supplement. Particularly advantageously, administration is in the form of a solution, for example in the form of prepared vials, or in the form of a powder. Because of its good solubility, collagen hydrolysate may also be added to different drinks without causing turbidity. The use of tasteless collagen hydrolysate may increase acceptance levels in users.

According to a preferred embodiment of the invention, apart from collagen hydrolysate the nutritional supplement contains no further proteins or protein hydrolysates. In known nutritional supplements for muscle development and muscle maintenance, various proteins are used, in particular by sportspeople, with the objective of replacing carbohydrates and fats to a large extent by proteins as suppliers of energy. However, use according to the invention is not based on the function of collagen hydrolysate as a supplier of energy but on the above-mentioned specific action on mitochondrial activity.

Accordingly, in a further embodiment of the invention, apart from collagen hydrolysate the nutritional supplement contains no further physiologically active constituents.

As an alternative, however, the invention also includes the case that collagen hydrolysate is administered as a constituent of a (nutritional) supplement having various further constituents. In particular, collagen hydrolysate may be added to a food or treat such as a chocolate bar, protein bar or cereal bar (so-called functional foods), or milk, dairy products (such as yoghurt) and milk substitutes (such as soy milk, almond milk and coconut milk).

Regardless of the form of administration, collagen hydrolysate is typically administered in a quantity of from 1 to 40 g per day, preferably from 2.5 to 30 g per day, more preferably from 10 to 25 g per day, and in particular from 12.5 to 20 g per day.

Where collagen hydrolysate is not used as the sole physiologically active constituent of a nutritional supplement, for use according to the invention it may be combined with one or more further components that have a positive effect on general health and in particular on endurance performance. Components of this kind are preferably selected from vitamin C, vitamins in the B, D, E and K series, conjugated linoleic acids, caffeine and derivatives thereof, guarana extract, green tea extract, epigallocatechin gallate, creatine, L-carnitine, L-citrulline, L-arginine, α-lipoic acid, N-acetylcysteine, NADH, D-ribose, magnesium aspartate, antioxidants such as anthocyanins, carotenoids, flavonoids, resveratrol, glutathione, superoxide dismutase and xanthans such as mangiferin, minerals such as iron, magnesium, calcium, zinc, selenium and phosphorus, and further proteins, hydrolysates or peptides such as soy, wheat or whey protein.

A further advantageous embodiment of the invention relates to combining collagen hydrolysate with ubiquinone-10 and/or ubiquinol, that is to say the oxidised and reduced forms of the coenzyme $Q_{10}$, wherein ubiquinol is preferred because of its better bioavailability. Even with a daily intake of 50 to 100 mg of ubiquinol, a positive effect on physical performance was observed, a promotion of mitochondrial activity by the antioxidant action of ubiquinol being assumed. In this way, the action of collagen hydrolysate in the case of the above-mentioned indications that are accompanied by mitochondrial dysfunction is thus supported. As an alternative or in addition, combining collagen hydrolysate with pyrroloquinoline quinone (PQQ), which has recently been discovered to be an important redox cofactor, is also possible.

In a particular embodiment of the invention, the administration of collagen hydrolysate is combined with endurance training or altitude training. Endurance training can enhance the aerobic capacity of the metabolism. It is further known that physical training in a relatively oxygen-depleted environment (hypoxic training) has a pronounced effect on endurance performance, so with a simultaneous dose of collagen hydrolysate a synergetic effect can be respectively expected. This is of particular interest to sportspeople.

On the other hand, within the scope of the invention it is likewise possible and indeed useful if the administration of collagen hydrolysate takes place in the absence of endurance training, altitude training or muscle training. In particular, it has been shown in animal tests (see below) that the effects according to the invention on mitochondrial activity and so on are already seen in combination with normal physical activity.

According to the invention, the molecular weight of the collagen hydrolysate used may vary within a broad range, wherein an upper limit is provided in that, unlike denatured collagen or gelatine, collagen hydrolysate has a sufficiently high degree of hydrolysis not to gel and to be water-soluble at room temperature. The soluble peptides of collagen hydrolysate can be resorbed into the body well. Typically, the collagen hydrolysate has an average molecular weight of from 200 to 25 000 Da, preferably from 1 000 to 6 000 Da, more preferably from 1 200 to 4 000 Da, even more preferably from 1 500 to 3 500 Da, and in particular from 2 800 to 3 300 Da.

Favourably, collagen hydrolysate is produced by enzymatic hydrolysis of a starting material containing collagen. For this hydrolysis in particular endopeptidases and/or exopeptidases of microbial or plant origin are used.

The collagen-containing starting material is typically selected from the skin or bones of vertebrates, preferably mammals, and in particular the skin of cattle or pigs (bovine split or pork rind). Collagen hydrolysate can either be produced in a one-step method from these starting materials, or by way of the intermediate stage of gelatine, in which case both type A gelatine and type B gelatine can be used.

As an alternative, collagen hydrolysate for use according to the invention may be produced by recombinant gene expression. By using natural collagen sequences, in particular from cattle or pigs, and the expression thereof in genetically modified cells (such as yeasts, bacteria or plant cells, in particular tobacco), products that are substantially identical to the hydrolysis products of the corresponding collagen-containing raw materials may be produced. Here, it is possible to obtain a relatively narrow or precisely predetermined distribution of molecular weights. As an alternative, the sequences may be altered by mutation in order to have an effect on particular properties of the product.

The present invention further relates to a method for improving the endurance performance and/or for stimulating lipid catabolism, in particular for reducing body weight, by increasing mitochondrial activity. The method preferably includes the enteral, in particular oral, administration of collagen hydrolysate to a person or an animal. The method may be a therapeutic method or indeed a non-therapeutic method.

The invention is explained in more detail with reference to in vitro and in vivo experimental results, which are described in the context of the examples below.

EXAMPLES

Example 1

Increasing the Number of Mitochondria Using Collagen Hydrolysate

It was possible to demonstrate the effectiveness of collagen hydrolysate for increasing the number of mitochondria in vitro with reference to human nerve cells (neuroblastoma cell line SH-SY5Y).

The SH-SY5Y cells were incubated in culture media with different concentrations of collagen hydrolysate, of 0.05 weight %, 0.2 weight % and 2.5 weight %. For this, a collagen hydrolysate from pork rind gelatine with an average molecular weight in the region of 3 000 Da, produced by enzymatic hydrolysis, was used (designated collagen hydrolysate A below). The molecular weight distribution of the peptides, which was determined by gel permeation chromatography, is shown in Table 1 below:

TABLE 1

Molecular weight distribution of collagen hydrolysate A

| Fraction | Weight % |
|---|---|
| >7 500 Da | <10 |
| 3 500-7 500 Da | 20-30 |
| 1 500-3 500 Da | 30-33 |
| 500-1 500 Da | 25-38 |
| 100-500 Da | <5 |

In order to enable direct evaluation of the number of mitochondria, the mitochondrial protein component TOM20 was fluorescence-labelled. TOM20 is a subunit of a receptor complex in the outer membrane of mitochondria, and has the function of moving cytosolic precursor proteins (prepeptides) into the mitochondria. There, the proteins, which are enzymes of the respiratory chain or the citric acid cycle, are activated by cleaving off the presequence.

Figure 1B:
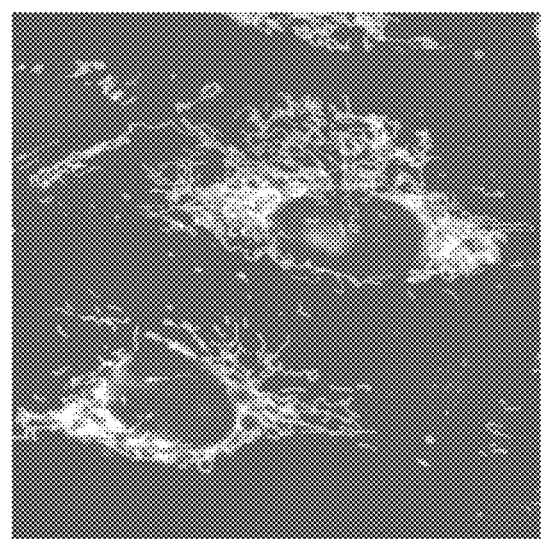
Figure 1C:
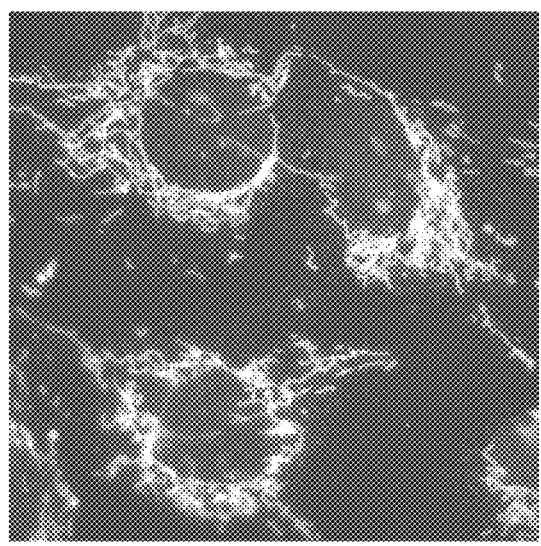

The quantity of fluorescence-labelled TOM20 that is visible under the fluorescence microscope is thus a measure of the number of mitochondria in the cell. The cells incubated with 0.05 weight %, 0.2 weight % and 2.5 weight % of collagen hydrolysate are shown in FIGS. 1A, 1B and 1C, where an increase in the pale fluorescence (green in the original) in the regions around the cell nucleus (blue in the original) as the concentration increases is clearly visible. Collagen hydrolysate thus brings about an increase in the number of mitochondria in the SH-SY5Y cells and hence an increase in the total mitochondrial activity.

Example 2

Activation of the Enzyme AMPK by Collagen Hydrolysate In Vitro

AMP-activated protein kinase (AMPK) is involved in the supply of energy in both the fatty tissue and the musculature. Since AMP is formed when ATP is consumed, it may be regarded as an indicator of an energy deficiency. The expression of AMPK thus serves to activate energy reserves from deposited fat and in the course of glycolysis.

In order to determine the effect of collagen hydrolysate on AMPK expression, human myocytes were incubated for a period of 24 hours in a medium containing 0.5 mg/ml of collagen hydrolysate. After removal of the medium, the RNA was extracted from the cell layer, and the quantity of AMPK-RNA was determined by PCR using specific primers.

In comparison with a control containing no collagen hydrolysate, the AMPK-RNA was significantly increased (by a factor of more than 600). From this finding as well, a stimulating effect on the energy metabolism of the cell by collagen hydrolysate is thus demonstrated.

Example 3

Activation of the Enzyme AMPK by Collagen Hydrolysate In Vivo

It was also possible to confirm the positive effect of collagen hydrolysate on AMPK expression using an animal test in vivo.

For this, mice were fed daily with a quantity of collagen hydrolysate corresponding to a human equivalent dose of 10 g, for a period of 3 months. After sacrifice of the mice, the quadriceps was completely excised, snap frozen and ground. The soluble proteins were extracted from the muscle tissue, and the quantity of AMPK was determined by immunoassay (ELISA).

In comparison with a control group that had received no collagen hydrolysate, the quantity of AMPK had increased by a factor of between 1.5 and 2.

Example 4

Effect of Collagen Hydrolysate on the Production of NADH In Vitro

The formation of the energy-rich form $NADH+H^+$ of nicotinamide adenine dinucleotide from the low-energy form $NAD^+$ is equivalent to the production of energy in the form of ATP. It is thus an indirect measure of mitochondrial activity in muscle cells.

For this test, human myocytes were incubated for a period of 6 days in a medium containing 0.5 mg/ml of collagen hydrolysate. Once the medium had been removed the triglycerides were extracted, and with the aid of the enzymes glycerol kinase and glycerol-3-phosphate dehydrogenase the energy in the triglycerides and the glycerol was determined in the form of the $NADH+H^+$ released.

In comparison with a control containing no collagen hydrolysate, the quantity of NADH had increased by a factor of approximately 2.

Example 5

Increasing the Mitochondrial Density in Rats In Vivo

In a preclinical study, it was possible to demonstrate a significant increase in mitochondrial density (that is to say an increase in the number and/or size of the mitochondria) in the skeletal musculature of rats as a result of the administration of different collagen hydrolysates.

The study was carried out on male rats of the CD® IGS line (Charles River Laboratories, Sulzfeld) which at the start of the period of the study were 64 days old and had a body weight of between 300 and 400 g. The test group and the control group each comprised six animals.

At the start of the study (t=0), a biopsy of the quadriceps femoris of each rat was taken by fine needle aspiration. Over a period of four weeks, the animals in the test groups then received a daily dose of 200 mg of the respective collagen hydrolysate (see below) per kg of current body weight (corresponding to a daily dose of 15 g in a human weighing 75 kg). The collagen hydrolysate was dissolved in an appropriate quantity of tap water at a concentration of 20 mg/ml and administered by way of a gastric tube. The animals in the control group each received an identical quantity of tap water containing no collagen hydrolysate.

Besides the collagen hydrolysate A described above, in further test groups there was used a collagen hydrolysate B of hide split gelatine with an average molecular weight of 2 000 Da, and a collagen hydrolysate C of hide split gelatine with an average molecular weight of 3 500 Da, in each case produced by enzymatic hydrolysis. The molecular weight distributions of all three hydrolysates are indicated in Table 2 below:

TABLE 2

Molecular weight distribution of collagen hydrolysates in weight %

| Fraction | Hydrolysate A | Hydrolysate B | Hydrolysate C |
| --- | --- | --- | --- |
| >7 500 Da | <10 | <3 | 4-14 |
| 3 500-7 500 Da | 20-30 | 10-20 | 18-25 |
| 1 500-3 500 Da | 30-33 | 25-32 | 30-38 |
| 500-1 500 Da | 25-38 | 40-50 | 28-36 |
| 100-500 Da | <5 | <15 | <7 |
| Average molecular wt | 3 000 Da | 2 000 Da | 3 500 Da |

After the end of the test period (t=4 w), all the rats were sacrificed, and a biopsy of the quadriceps femoris was again taken by fine needle aspiration. During the four weeks, there was an average increase in weight of the rats of approximately 30%, there being no significant difference between the test group and the control groups.

In order to determine the mitochondrial density, the biopsies taken before and after the test period were prepared for analysis with a transmission electron microscope, as described in the literature (see A. Glauert and P. Lewis: Biological Specimen Preparation for Transmission Electron Microscopy, Princeton Legacy Library, 2014). In each case, individual surface portions of the muscle biopsies 15.17× 15.17 µm in size (230 µm$^2$) were digitalised and evaluated semi-quantitatively. Here, the average surface area of the mitochondria as a proportion of the total surface area was determined using 10 individual samples from each biopsy. It was possible to locate the mitochondria from the clearly visible characteristic structure of the inner membrane with its cristae.

Table 3 below shows the development of mitochondrial density (µm$^2$ mitochondria per 230 µm$^2$ total surface area) in the animals in the test group with collagen hydrolysate A:

TABLE 3

Development in test group A over time

| Rat number | Test group A, t = 0 | Test group A, t = 4 w |
| --- | --- | --- |
| 1 | 9.82 | 11.97 |
| 2 | 10.36 | 17.44 |
| 3 | 6.84 | 12.36 |

TABLE 3-continued

Development in test group A over time

| Rat number | Test group A, t = 0 | Test group A, t = 4 w |
| --- | --- | --- |
| 4 | 8.15 | 17.46 |
| 5 | 8.03 | 15.61 |
| 6 | 6.18 | 13.29 |
| Mean value | 8.23 | 14.69 |
| Standard deviation | ±1.63 | ±2.48 |

The results showed that a four-week administration of collagen hydrolysate A resulted in a very clear increase in mitochondrial density, by an average of 78.5%, which is also statistically significant (p=0.001).

A similar finding was also demonstrated by a comparison of mitochondrial density between the test groups with collagen hydrolysates A, B and C and the control group, in each case after 4 weeks, in accordance with Table 4 below:

TABLE 4

Comparison of test groups A, B and C and control group

| Rat number | Control group, t = 4 w | Test group A, t = 4 w | Test group B, t = 4 w | Test group C, t = 4 w |
| --- | --- | --- | --- | --- |
| 1 | 8.95 | 11.97 | 15.06 | 14.66 |
| 2 | 6.84 | 17.44 | 15.11 | 18.76 |
| 3 | 11.73 | 12.36 | 16.09 | 19.97 |
| 4 | 8.76 | 17.46 | 13.39 | 16.53 |
| 5 | 9.74 | 15.61 | 15.43 | 19.72 |
| 6 | 10.28 | 13.29 | 14.65 | 17.56 |
| Mean value | 9.38 | 14.69 | 14.96 | 17.86 |
| Standard deviation | ±1.64 | ±2.48 | ±0.90 | ±2.04 |

In the test groups, the mitochondrial density was on average 56.6% (A), 59.5% (B) and 90.4% (C) higher than in the control group, which is likewise statistically significant (p=0.001). The Cohen's d value, as a measure of the effect size, is more than 2.5 for all test groups, so in each case there is a very pronounced effect.

To summarise, this study provides unambiguous proof that the administration of collagen hydrolysate results in a significant increase in the mitochondrial density in muscle cells and thus also in a corresponding increase in mitochondrial activity. This effect can be confirmed with collagen hydrolysates of different origins (pigs and cattle) and molecular weight distributions.

The invention claimed is:

1. A method for improving endurance performance by increasing mitochondrial activity in a person or animal, the method including oral administration of from 12.5 to 20 g of collagen hydrolysate to the person or animal per day in the form of a nutritional supplement, wherein the collagen hydrolysate is produced by enzymatic hydrolysis of a collagen-containing starting material selected from the skin or bones of vertebrates.

2. The method according to claim 1, wherein apart from collagen hydrolysate the nutritional supplement contains no further proteins or protein hydrolysates.

3. The method according to claim 1, wherein the collagen hydrolysate is combined with one or more components that are selected from vitamin C, vitamins in the B, D, E and K series, conjugated linoleic acids, caffeine and derivatives thereof, guarana extract, green tea extract, epigallocatechin gallate, creatine, L-carnitine, L-citrulline, L-arginine, α-lipoic acid, N-acetylcysteine, NADH, D-ribose, magnesium aspartate, antioxidants such as anthocyanins, carotinoids, flavonoids, resveratrol, glutathione, superoxide dismutase and xanthones such as mangiferin, minerals such as iron, magnesium, calcium, zinc, selenium and phosphorus, and further proteins, hydrolysates or peptides such as soy, wheat or whey protein.

4. The method according to claim 1, wherein the collagen hydrolysate is combined with ubiquinone-10, ubiquinol, pyrroloquinoline quinone (PQQ), or mixtures thereof.

5. The method according to claim 1, wherein the administration of collagen hydrolysate is combined with endurance training or altitude training.

6. The method according to claim 1, wherein the administration of collagen hydrolysate takes place in the absence of endurance training, altitude training or muscle training.

7. The method according to claim 1, wherein the collagen hydrolysate has an average molecular weight of from 1,200 to 4,000 Da.

8. The method according to claim 7, wherein the collagen hydrolysate has an average molecular weight of from 2,800 to 3,300 Da.

\* \* \* \* \*